(12) United States Patent
Solotoff

(10) Patent No.: US 11,857,449 B1
(45) Date of Patent: Jan. 2, 2024

(54) COMPRESSION BRACES WITH REMOVABLE HOT/COLD PACKS

(71) Applicant: PREFERRED PRESCRIPTION, INC., Hollywood, FL (US)

(72) Inventor: Brandon Solotoff, Boca Raton, FL (US)

(73) Assignee: Preferred Prescription, INC., Hollywood, FL (US)

( * ) Notice: Subject to any disclaimer, the term of this patent is extended or adjusted under 35 U.S.C. 154(b) by 624 days.

(21) Appl. No.: 16/990,038

(22) Filed: Aug. 11, 2020

Related U.S. Application Data

(60) Provisional application No. 62/887,150, filed on Aug. 15, 2019, provisional application No. 62/899,277, (Continued)

(51) Int. Cl.
*A61F 5/01* (2006.01)
*A61F 7/02* (2006.01)
*A61F 7/00* (2006.01)

(52) U.S. Cl.
CPC .............. *A61F 5/0125* (2013.01); *A61F 7/02* (2013.01); *A61F 2005/0144* (2013.01); (Continued)

(58) Field of Classification Search
CPC ...... A61F 7/02; A61F 7/08; A61F 7/10; A61F 5/01–0109; A61F 5/0123; A61F 5/0125; (Continued)

(56) References Cited

U.S. PATENT DOCUMENTS 1,258,052 A 3/1918 Stall
1,510,408 A 9/1924 Lychou
(Continued)

FOREIGN PATENT DOCUMENTS

AU 714588 B2 1/2000
CA 2233483 C 4/1997
(Continued)

OTHER PUBLICATIONS

Press Fit Forces Stress Design Calculator, Jun. 18, 2018, available at: www.engineersedge.com/calculators/machine-design/press-fit/press-fit.htm.
(Continued)

*Primary Examiner* — Michelle J Lee
*Assistant Examiner* — Daniel A Miller
(74) *Attorney, Agent, or Firm* — Thomas A. O'Rourke; Bodner & O'Rourke, LLP

(57) ABSTRACT

A knee brace includes: an elastic sleeve; first and second stiffening members coupled together to crisscross to form an X-shape, and secured to a medial side of the sleeve; third and fourth stiffening members similarly coupled together and secured to a lateral side of the sleeve; and a plurality of slits in the sleeve into a corresponding pockets that receive a thermal pack. The thermal packs and pockets are triangular shaped, with two triangular-shaped pockets on the medial side of the sleeve, and two on the lateral side, each disposed in a respective triangular shape positioned between the x-shape of the stiffening members. The pairs of stiffening members are either: fixedly coupled together to store energy when the user bends at the knee, and to expend the stored energy to assist in lifting the user upward; or pivotally coupled together to pivot according to movements of the wearer's knee joint.

12 Claims, 12 Drawing Sheets

Related U.S. Application Data filed on Sep. 12, 2019, provisional application No. 62/934,591, filed on Nov. 13, 2019, provisional application No. 62/934,587, filed on Nov. 13, 2019.

(52) U.S. Cl.
CPC .............. *A61F 2005/0197* (2013.01); *A61F 2007/0041* (2013.01); *A61F 2007/0042* (2013.01); *A61F 2007/0043* (2013.01); *A61F 2007/023* (2013.01); *A61F 2007/0226* (2013.01)

(58) Field of Classification Search
CPC ...... A61F 2005/0144; A61F 2005/0197; A61F 2007/0041; A61F 2007/0042; A61F 2007/0043; A61F 2007/023; A61F 2007/0233; A61F 2007/0226; A61F 3/00; A41D 1/215
USPC .......................................................... 602/14
See application file for complete search history.

(56) References Cited

U.S. PATENT DOCUMENTS

| | | |
|---|---|---|
| 1,567,931 A | 12/1925 | Epler |
| 1,622,211 A | 3/1927 | Sheehan |
| 2,270,685 A | 1/1942 | Miller |
| 2,467,907 A | 4/1949 | Peckham |
| 2,547,886 A | 4/1951 | Poux |
| 2,907,173 A | 10/1959 | Robbins |
| 3,046,981 A | 7/1962 | Biggs |
| 3,075,529 A | 1/1963 | Young |
| 3,084,685 A | 4/1963 | Lewis |
| 3,327,703 A | 6/1967 | Gamm |
| 3,506,013 A | 4/1970 | Zdenek |
| 3,551,912 A | 1/1971 | Viglione |
| 3,587,572 A | 6/1971 | Evans |
| 3,822,705 A | 7/1974 | Pilotte |
| 3,889,684 A | 6/1975 | Lebold |
| 3,900,035 A | 8/1975 | Welch |
| 3,945,046 A | 3/1976 | Stromgren |
| 4,084,506 A | 4/1978 | Nakatani |
| 4,116,236 A | 9/1978 | Albert |
| 4,176,665 A | 12/1979 | Terpening |
| 4,201,203 A | 5/1980 | Applegate |
| 4,204,543 A | 5/1980 | Henderson |
| 4,219,892 A | 9/1980 | Rigdon |
| 4,240,414 A | 12/1980 | Theisler |
| 4,275,716 A | 6/1981 | Scott, Jr. |
| 4,287,885 A | 9/1981 | Applegate |
| 4,353,362 A * | 10/1982 | DeMarco ............ A61F 5/0109 D24/190 |
| 4,366,813 A | 1/1983 | Nelson |
| 4,370,978 A | 2/1983 | Palumbo |
| 4,387,709 A | 6/1983 | Shen |
| 4,445,505 A | 5/1984 | Labour |
| 4,527,566 A | 7/1985 | Abare |
| 4,585,003 A | 4/1986 | Meistrell |
| 4,586,506 A | 5/1986 | Nangle |
| 4,607,628 A | 8/1986 | Dashefsky |
| 4,628,932 A | 12/1986 | Tampa |
| 4,671,267 A | 6/1987 | Stout |
| 4,688,572 A | 8/1987 | Hubbard |
| 4,753,240 A | 6/1988 | Sparks |
| 4,832,371 A | 5/1989 | Mugnai |
| 4,870,956 A | 10/1989 | Fatool |
| 4,872,448 A | 10/1989 | Johnson |
| 4,908,037 A | 3/1990 | Ross |
| 4,938,207 A | 7/1990 | Vargo |
| 4,972,832 A | 11/1990 | Trapini |
| 4,976,262 A | 12/1990 | Palmacci |
| 5,000,176 A | 3/1991 | Daniel |
| 5,016,621 A | 5/1991 | Bender |
| 5,074,285 A | 12/1991 | Wright |
| 5,077,837 A | 1/1992 | Meistrell |
| 5,088,487 A | 2/1992 | Turner |
| 5,111,810 A | 5/1992 | Fortney |
| 5,133,348 A | 7/1992 | Mayn |
| 5,139,477 A | 8/1992 | Peters |
| 5,148,804 A | 9/1992 | Hill |
| 5,215,080 A | 6/1993 | Thomas |
| 5,277,697 A | 1/1994 | France |
| 5,314,455 A | 5/1994 | Johnson |
| 5,395,399 A | 3/1995 | Rosenwald |
| 5,398,667 A | 3/1995 | Witt |
| 5,415,624 A | 5/1995 | Williams |
| 5,446,251 A | 8/1995 | Lin |
| 5,728,058 A | 3/1998 | Ouellette et al. |
| 5,728,147 A | 3/1998 | Thomas |
| 5,792,084 A | 8/1998 | Wilson |
| 5,800,490 A | 9/1998 | Patz |
| 5,857,988 A | 1/1999 | Shirley |
| 5,860,945 A | 1/1999 | Cramer |
| 5,865,776 A | 2/1999 | Springs |
| 5,865,777 A | 2/1999 | Detty |
| 5,873,848 A | 2/1999 | Fulkerson |
| 5,873,903 A | 2/1999 | Garcia |
| 6,598,235 B2 | 7/2003 | Bulla |
| 6,773,411 B1 | 8/2004 | Alvarez |
| 7,004,919 B2 | 2/2006 | Gaylord |
| 7,060,086 B2 | 6/2006 | Wilson |
| 7,127,249 B2 | 10/2006 | Miernik |
| D573,713 S | 7/2008 | Mueller |
| 7,713,225 B2 | 5/2010 | Ingimundarson |
| D634,437 S | 3/2011 | Gramza |
| 7,896,827 B2 | 3/2011 | Ingimundarson |
| D818,138 S | 5/2018 | Nicosia |
| 10,555,863 B2 | 2/2020 | Hall |
| 2003/0083605 A1 | 5/2003 | Edmund |
| 2003/0176826 A1 | 9/2003 | Scott |
| 2004/0225245 A1 | 11/2004 | Nelson |
| 2011/0224762 A1 | 9/2011 | Gruber |
| 2011/0257575 A1 | 10/2011 | Farrow |
| 2017/0027734 A1 | 2/2017 | Riordan |
| 2017/0304112 A1 * | 10/2017 | Burstein ............ A61F 7/10 |
| 2018/0078398 A1 | 3/2018 | Ingimundarson |

FOREIGN PATENT DOCUMENTS

| | | |
|---|---|---|
| EP | 0860153 A1 | 8/1998 |
| WO | WO2008077112 A2 | 6/2008 |

OTHER PUBLICATIONS

"Three General Types of Fit," available at www.mmto.org/dclark/Reports/Encoder%20Upgrade/fittolerences%20%5BRead-Only%5D.pdf., Jul. 8, 2019.

"Engineering Fit," available at: https://en.wikipedia.org/wiki/Engineering_fit, Jul. 8, 2019.

* cited by examiner

COMPRESSION BRACES WITH REMOVABLE HOT/COLD PACKS

CROSS REFERENCES TO RELATED APPLICATIONS

This application claims priority on U.S. Provisional Application Ser. No. 62/887,150, filed on Aug. 15, 2019; 62/899,277, filed on Sep. 12, 2019; 62/934,591, filed on Nov. 13, 2019; and 62/934,587, filed on Nov. 13, 2019; all disclosures of which are incorporated herein by reference.

FIELD OF THE INVENTION

The subject technology relates generally to braces, particularly compression braces, which may be used on a body when compression and/or heat or cold treatment is desired. The brace of the present invention may, for example, be configured to support a joint that may be injured or weakened or to support and protect a healthy joint from being injured particularly during sporting events. The article of the present invention is not limited to braces but can be any compression product that is positioned on the body and which provides the application of heat or cold to an area of the body. The subject technology more particularly relates to a brace that provides both support and hot or cold treatments to a joint and surrounding area, which may be adapted for use at any area of the body, including but not limited to, the knee joint, the elbow joint, the ankle joint, and the wrist joint, etc.

BACKGROUND OF THE INVENTION

One of the problems encountered in providing compression braces with openings for receiving hot or cold packs is avoiding tearing or ripping of the material. Many compression braces made of elastic based fabrics or other elastic materials. Many of these elastic materials used for compression braces are multi-layered structures where there is a slit in the outer or elastic surface of the material. The ends of the slit provide a weak point where the tear or slit can propagate to rip or cause the material to lose its compressibility.

Another issue with many braces that apply heat or cold to a site on the body is how the heat or cold pack is held in position in the brace so that it can provide the requisite heat or cold to the body at the selected location.

Many of these prior compression braces that apply heat or cold to the body have a two or more layer structure with the compression fabric on the outer surface of the structure. A non-compressive fabric is the inner layer, the layer adjacent to the user's skin. This inner fabric layer has an opening for receiving the ice or heat pack. Thus, the compression fabric does not have any cuts or slits in the compression fabric to receive the ice or heat pack. Cuts in the compression fabric can cause the compression fabric to lose some or all of its compressibility. The cuts in the surface for the hot or cold packs can also lead to tears in the compression fabric.

OBJECTS OF THE INVENTION

It is an object of the invention to provide a compression article such as a brace that will provide heat or cold to a part of the body where such treatment is desired.

It is an object of the invention to provide a brace to support a joint of a wearer.

It is another object of the invention to provide a brace that both supports the joint of the wearer and also provide relief to the pain experience at the person's joint.

It is a further object of the invention to provide a brace that support the wearer's joint and permits the application of heat or cooling to the region.

It is another object of the invention to provide a brace that supports a joint of a wearer and which also has pockets to quickly and easily insert and remove hot and cold pouches to apply heat and cooling treatments to the wearer's joint.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

An improved knee brace includes: a sleeve, made of an elastic material (i.e., lycra, rubber, latex, etc.), and formed to fit on a leg of a wearer, and to extend a distance above the knee and extend a second distance below the knee. The brace also includes a first stiffening member and a second stiffening member, which stiffening members are coupled together to crisscross to form an X-shape; and where the coupled first and second stiffening members are secured to a medial side of the sleeve, with the crisscross portion of the x-shape being centered proximate to a knee joint portion of the sleeve. Third and fourth stiffening members are similarly coupled together and secured to a lateral side of the sleeve with its crisscrossed x-shape being positioned centered proximate to the knee joint portion of the sleeve. The sleeve also has a plurality of slits in the sleeve into a corresponding plurality of pockets; and a plurality of thermal packs, with one of the thermal packs received in a respective one of the plurality of pockets.

The thermal packs used in the knee brace are triangular shaped, and the plurality of pockets are each correspondingly triangular-shaped and respectively sized to receive one of the triangular shaped thermal packs therein in a clearance fit.

The knee brace may have only two pockets, on each of the lateral and medial sides, or may alternatively have four of the triangular-shaped pockets, two of the triangular-shaped pockets on the medial side of the sleeve, and two of the triangular-shaped pockets on the lateral side of the sleeve; where two of the triangular-shaped pockets are disposed in a respective triangular shape positioned between the x-shape of the first and second stiffening members; and two of the triangular-shaped pockets are disposed in a respective triangular shape positioned between the x-shape of the third and fourth stiffening members.

The first and second stiffening members may be fixedly coupled together to store energy when the user bends at the knee, and to utilize the stored energy to assist in lifting the user upward; and alternatively, the first and second stiffening members may be pivotally coupled together, to pivot with respect to each other according to movements of the wearer's upper leg portion and lower leg portion at the knee joint.

Each thermal pack is formed with a tab protruding from a base of the triangular shape, to assist in removal of the thermal pack from the pocket, which may otherwise be difficult because of the compressive force applied by the elastic sleeve.

The slit into the pockets of the sleeve may have a reinforcement material applied to the area surrounding the slit. The reinforcement material may be any one or more of: a grommet, an eyelet, stitching, one or more rivets, a printed silicon, and plastic material.

Each pocket may be formed with a liner, which may include a mesh material. The mesh material may be a thermoplastic elastomer or a thermoplastic polyurethane. The coupled first and second stiffening members and the coupled third and fourth stiffening members are each respectively secured to the sleeve by one or more methods, including: by being adhesive bonded thereto; by being sewn to the side of the sleeve between an outer layer and an inner layer of the sleeve; and by positioning a respective cover layer over the stiffening members and stitching the respective cover layer to the sleeve.

BRIEF DESCRIPTION OF THE DRAWINGS

The description of the various example embodiments is explained in conjunction with appended drawings, in which.

Figure 1:
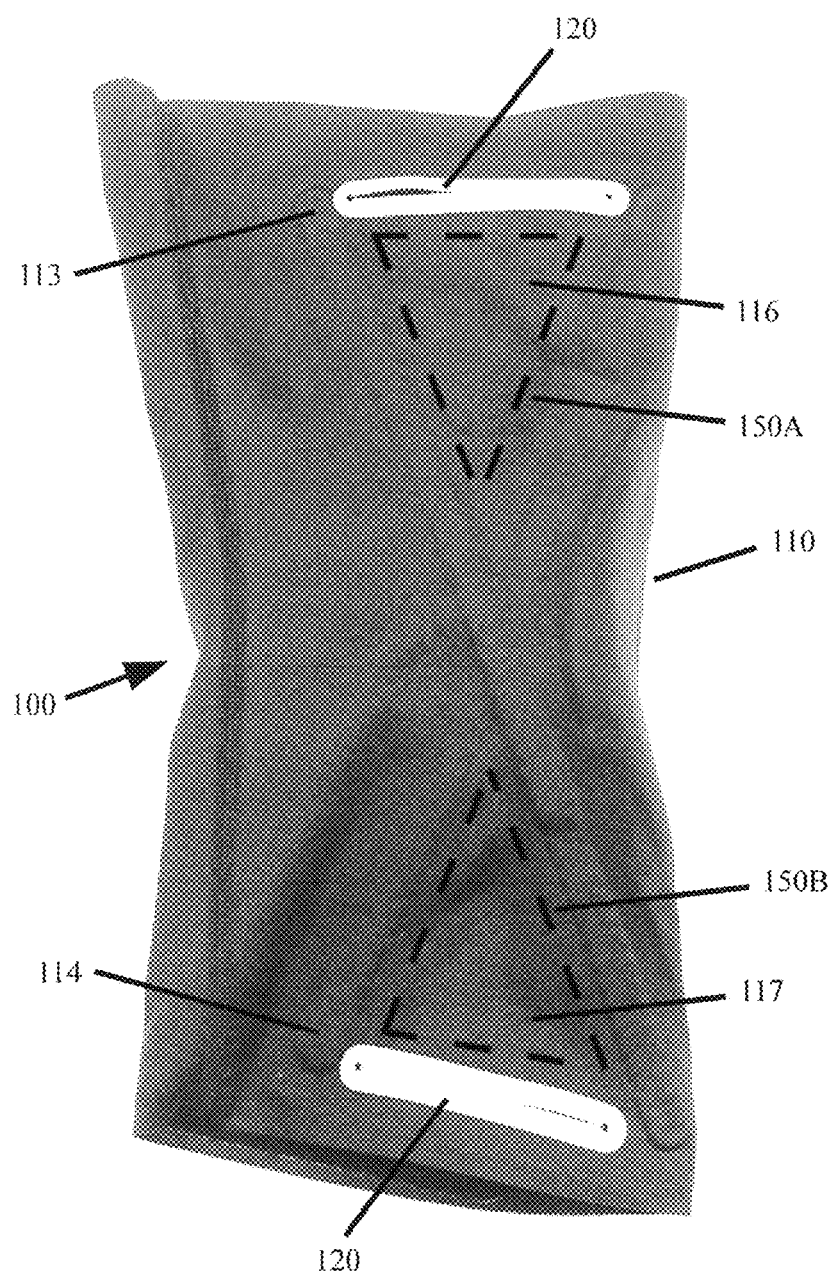
FIG. 1 is a front perspective view showing the brace configured for use on, for example, a knee of a leg, with reinforced, slotted openings for two outer pockets being shown to receive hot/cold packs to be placed and secured within the pockets.

It will be appreciated by one skilled in the art that although a knee brace is shown in the Figures, the concepts of the present invention apply to any compression brace no matter where positioned on a patient.

DETAILED DESCRIPTION OF THE INVENTION

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed apparatus.

Furthermore, the described features, advantages, and characteristics of any particular embodiment disclosed herein, may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations (see e.g., "Press Fit Engineering and Design Calculator," available at: www.engineersedge.com/calculators/machine-design/press-fit/press-fit-calculator.htm).

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit (e.g., for a 0.1250 inch shaft diameter the opening may be 0.1285 inches for a close fit and may be 0.1360 inches for a free (running) fit; and for a 0.5000 inch diameter shaft size the opening may be 0.5156 inches for a close clearance fit and may be 0.5312 inches for a free clearance fit). Other clearance amounts may also be used.

Figure 7:
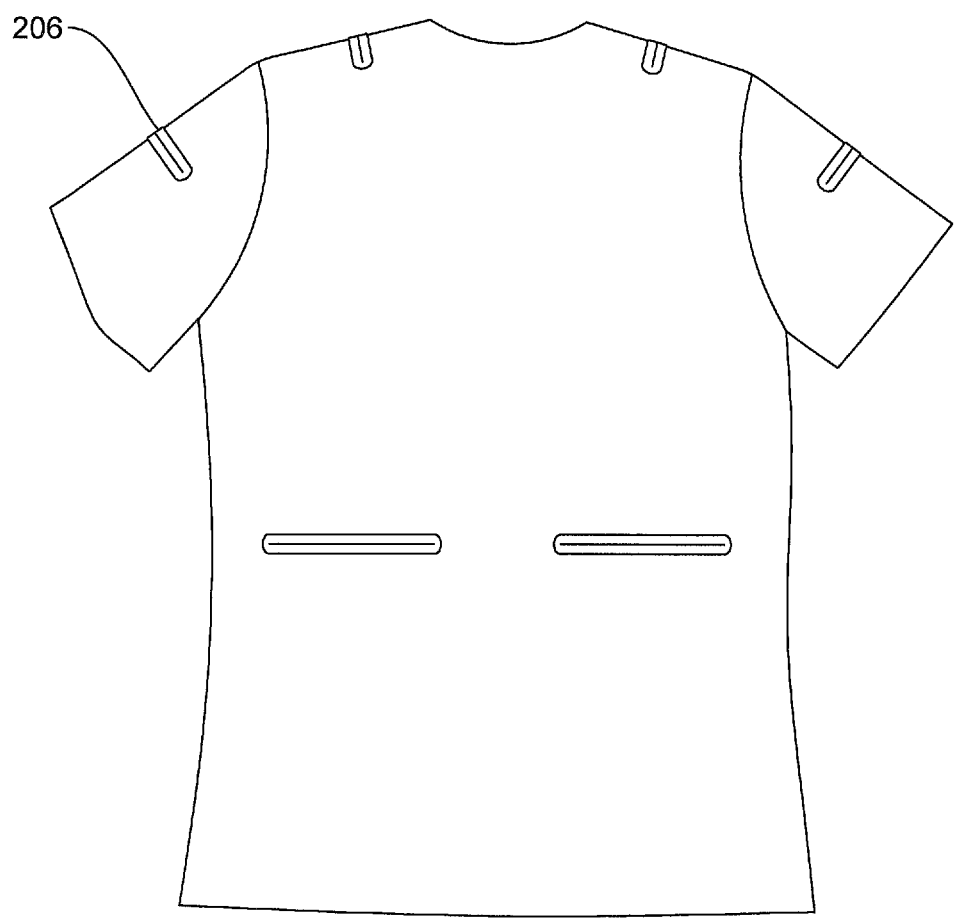
FIG. 7 is an example of a compression shirt having a plurality of slits for inserting heat or cold packs.
Figure 8:
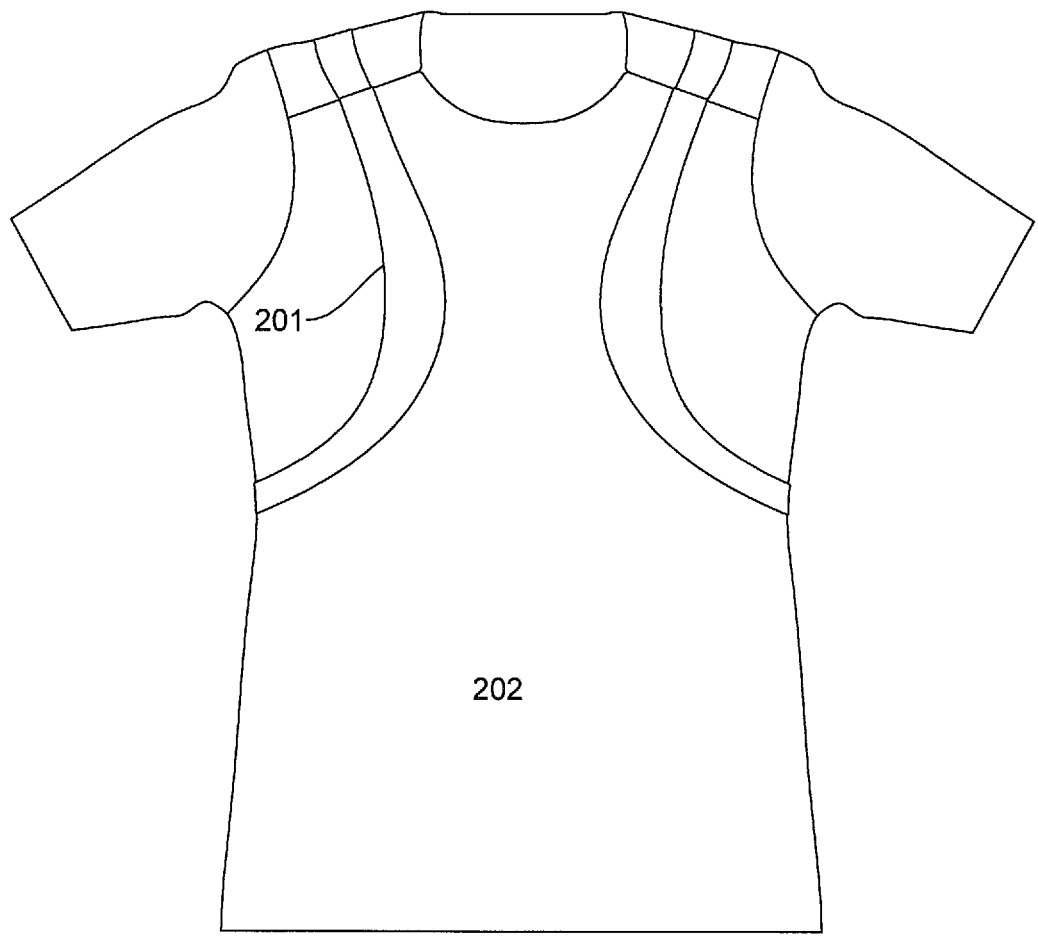
FIG. 8 is an example of a shirt having an area of high compression shown in black and a second area of a lighter material that has either no compressive effect or a lesser compression.

In accordance with at least one embodiment, a brace 100 as shown in FIG. 1 may broadly include a sleeve 110 formed of an elastic material, and may include one or more stiffening members that may be in the form of a spring. The elastic material used for the sleeve 110 may include, but is not limited to, lycra, rubber, latex, etc. The elastic material may comprise substantially an entire layer of the article, see FIG. 7, or it may comprise one or more regions of elasticity in the layer along with areas of a different elasticity, see FIG. 9. In a still further embodiment, there may be one or more strips of high compression material and regions of low compression material in the article, see FIG. 8. Preferably, in one embodiment, the strips of compression material do not have a free end. The strips of compression material may also be fan shaped wherein there is one end and each of the strips extend outwardly from that common end point. The free ends of the compression strips should be attached to another free end of a compression strip and not a material with less compression. This will help prevent the higher compression material from pulling the lower compression material and possibly ripping or tearing it. As seen in FIG. 8 the compressive strip 201 is comprised of a plurality of strips secured generally end to end to form a continuous strip that preferably has no free end.

In a preferred embodiment the compression sleeve may have a plurality of layers. One layer, preferably the outer layer, may be made of a compression material. It will be appreciated that the compression layer may have a layer over it so it is not the outer surface. This may be a decorative material. This compression material may have areas of one amount of compression, as well as one or more areas of higher compressive forces. See FIG. 8 where the high compression material 201 has a greater compressive force than the remaining area 202. By compression it meant a material that has a resting configuration that can be expanded through the use of a force to a larger size, and wherein the elastic material tries to return to its original configuration when the force is released. The compression material can be used in a variety of ways, including but not limited to, limiting the movability of a limb in one or more directions, provide support for weakened parts of the body or force areas of the body into a desired position, etc.

The compression article may have one or more additional layers accompanying the compressive layer. These layers can be a body contact layer which may be made of any suitable material that aids in the user's comfort, for example. Other materials may be used to provide a wicking capability to draw moisture away from the skin or a material that has a coefficient of friction such that when it contacts the skin, the material renders it easy to position the limb or portion of the body. The inner layer may be made from any material depending on what properties are desired by the user or a medical practitioner.

Figure 12:
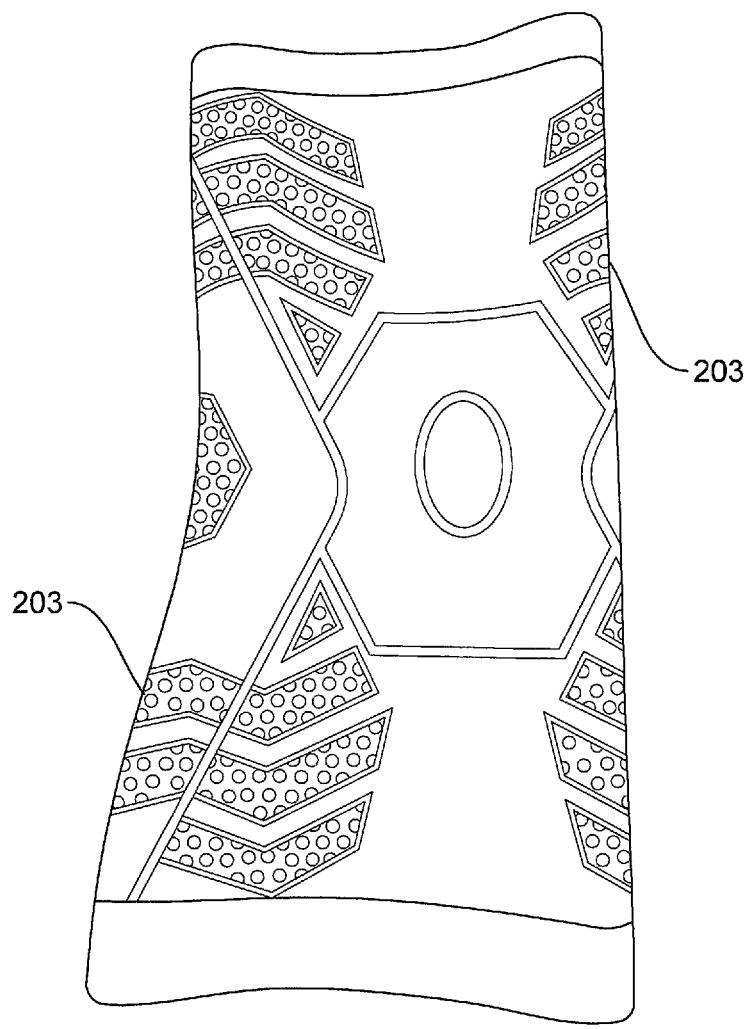
FIG. 12 shows an alternate embodiment where the high compression region is in the form of a decorative compressive material.

In a preferred embodiment there may also be a mesh material comprised of a TPE (Thermoplastic elastomer) or TPU (Thermoplastic polyurethane) as a layer. The mesh material due to its porosity provides a path for the heat or cold to reach the body contact layer and the body, as well. The TPE or TPU material can be the compression material or a separate layer. When TPE or TPU is present, it is preferably a separate layer and it is preferably in the form of a mesh layer. The mesh layer can be positioned between the compression layer and the body contact layer. As seen in FIG. 12 there can be a mesh material 203 that adds compressibility to selected areas of the compression layer by being positioned over the compression layer.

The brace 100 may also include padding in key locations that may be made of any suitable material including, but not limited to, silicone or other cushioning material, which may be added therein using a suitable process such as a high frequency pressing process. The spring can be any resilient material that one or more portions thereof can be bent or deflated from its original position and wherein it returns to its original configuration.

The elastic sleeve 110 may be formed to fit over the knee area of the wearer's leg, and may thus be generally hourglass shaped, having a narrow central region that may gradually widen toward each of the ends—i.e., towards the first end 111 and the second end 112 of the sleeve. Other shapes are used for other body locations as necessary.

The elastic sleeve 110 may be formed to include a first stiffening member 113 and a second stiffening member 114, each of which may be an elongated flat member (i.e., a leaf spring) that may be secured to the sleeve. In one embodiment the first stiffening member 113 and second stiffening member 114 may each be adhesive bonded to a side of the elastic sleeve 110. In other embodiments the first stiffening member 113 and second stiffening member 114 may each secured to the side of the elastic sleeve 110 by being sewn to the side of the sleeve, by being sewn between an outer layer and an inner layer, or by having a cover material positioned over the stiffening member and being stitched to the side of the elastic sleeve.

As seen in FIG. 1, the first stiffening member 113 and second stiffening member 114 may be oriented to crisscross and form an X-shape. The first stiffening member 113 may be pivotally coupled to the second stiffening member 114 where the members cross, and in one embodiment may generally pivot with respect to each other according to movements of the wearer's upper leg portion (the lower thigh) and lower leg portion (the upper calf) at the knee joint. In another embodiment the first stiffening member 113 may be fixedly secured to the second stiffening member 114 to provide a reaction to assist the wearer who has bent down in standing back up, and assist in lifting themselves upward, and thus may store energy.

The elastic sleeve 110 may be formed to include at least one pocket that may be sized and shaped to receive a correspondingly sized/shaped hot and/or cold pack therein, to apply heat and/or cooling therapy to the injured knee region. Such hot/cold packs are known in the art, as shown for example by the following U.S. Pat. No. 2,907,173 to Robbins; U.S. Pat. No. 3,175,558 to Caillouette; U.S. Pat. No. 3,342,324 to Piazze; U.S. Pat. No. 3,542,032 to Spencer; U.S. Pat. No. 3,804,077 to Williams; U.S. Pat. No. 4,462,224 to Dunshee; and U.S. Pat. No. 5,792,213 to Bowen.

In addition, the following U.S. Patents disclose hot/cold packs that may be used herein, and which are configured for reuse, as they may be heated in a microwave or cooled by being placed in a refrigerator/freezer: U.S. Pat. No. 3,889,684 to Lebold; U.S. Pat. No. 4,462,224 to Dunshee; U.S. Pat. No. 4,700,706 to Munch; U.S. Pat. No. 5,190,033 to Johnson; and U.S. Pat. No. 5,843,145 to Brink. The pack does not have to be heated or cooled but can be room temperature. At this temperature the pack insertion increases the amount of compression or the area of the body where the pocket is.

Figure 9:
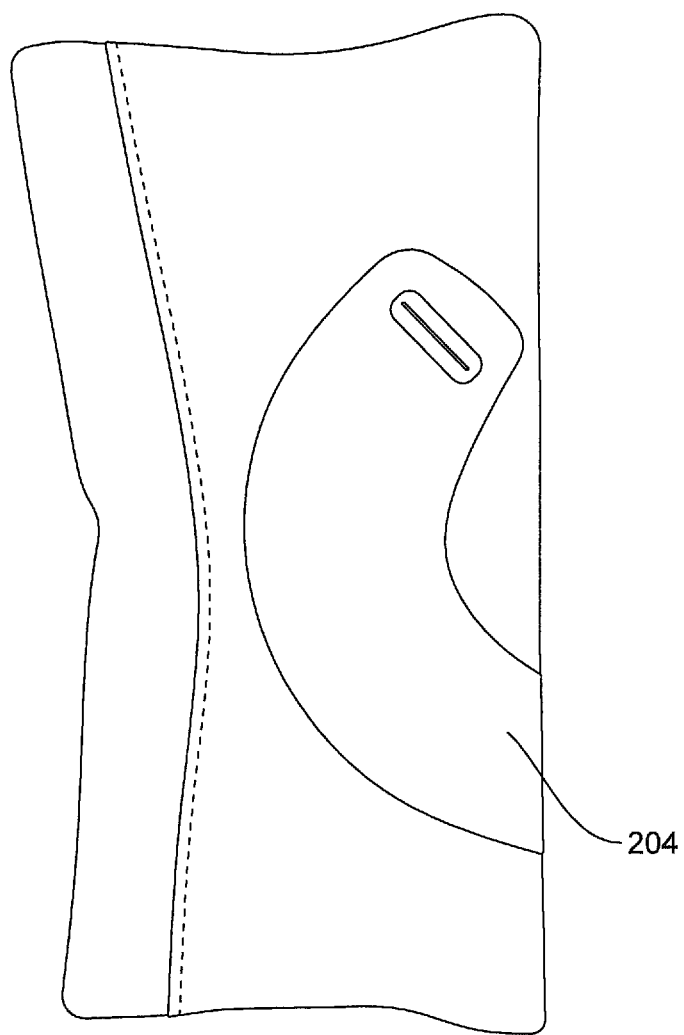
FIG. 9 shows a brace with a high compression area that has a circular configuration with a different compressive strength in the center of the circle and outside of the circular high compression region.
Figure 10:
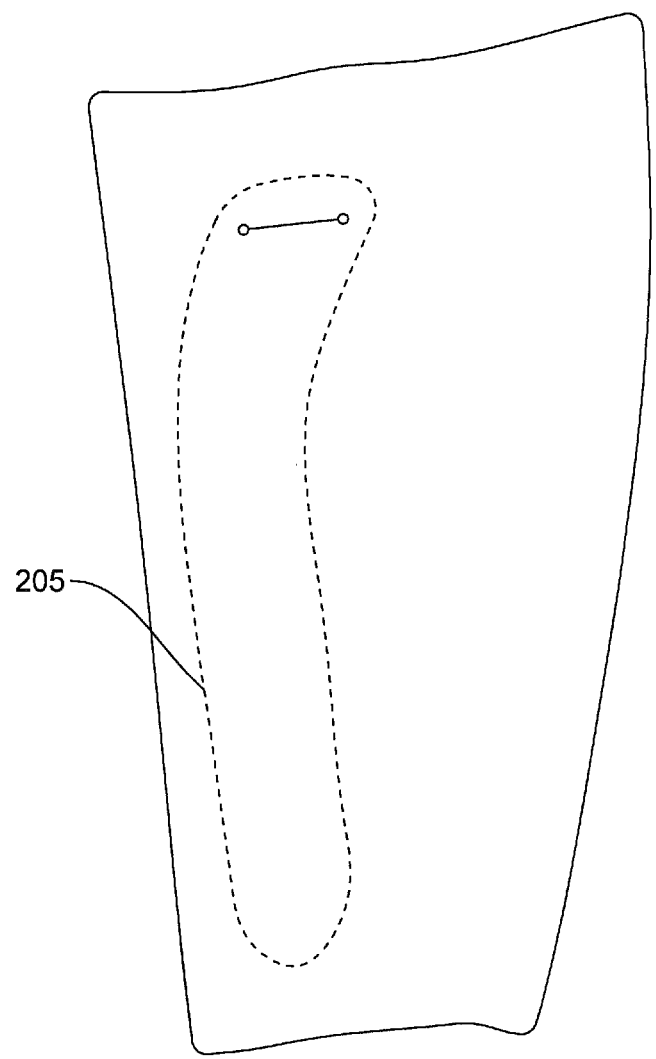
FIG. 10 shows an alternate arrangement for the pocket and the slit.
Figure 11:
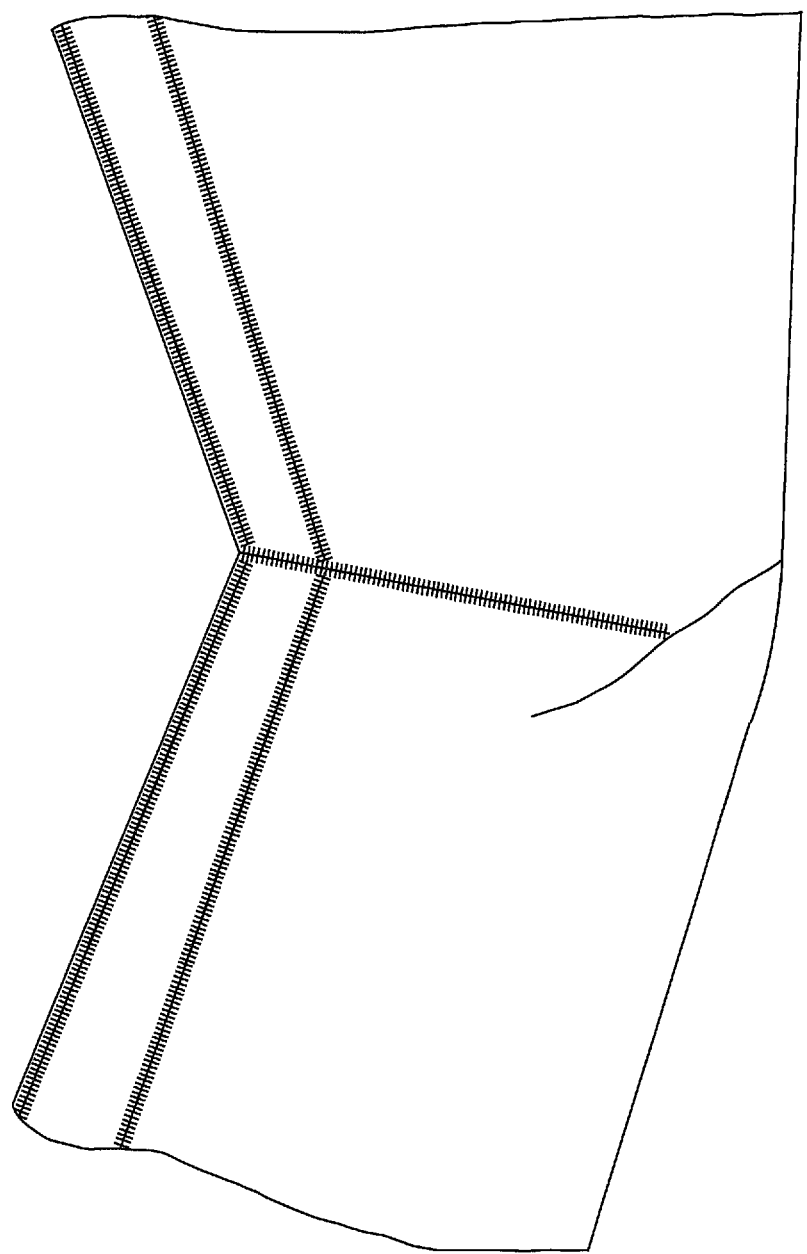
FIG. 11 shows an alternate means of creating a high compression region through the use of stitching.

In a preferred embodiment the brace may have a slit in the outer surface of the compression material. This slit is the opening to a pocket formed in the sleeve for receiving the hot/cold pack. The pocket is preferably shaped to receive a correspondingly shaped heat or cold pack. The pocket and the heat or ice pack are preferably of similar shape. The heat or ice pack preferably has an angular end like a pointed tip that makes it easier to insert the pack into the pocket or pouch. A preferred shape is one with a pointed end that renders it easy to insert with a single hand. FIGS. 9 and 10 show examples of braces where different shaped pockets are present. These pockets would receive one or more correspondingly shaped packs. In FIG. 9 a circular area is shown for applying heat or cold. There could be a corresponding slit on the opposite side of the brace to receive an arcuate heat or cold pack corresponding to the region 204 shown in FIG. 9. FIG. 10 shows another example of a compression brace where there is a pocket and a slit. The pocket may be a separate member in the structure. The pocket can also be an area in the article where thread or adhesive is applied to the article to form a pocket in the article. See FIG. 10 where the pocket 205 is formed by thread by sewing the outer compression layer to an adjacent layer. For example, a portion of the compression layer can be secured to a portion of the adjacent layer to form a pocket.

The slit is preferably positioned in the compression material layer to avoid any section with high compression material in the brace. The area around the brace preferably has an area of reinforcement around the opening formed by the slit. See FIG. 6. This reinforcement 206 can be a fabric or other suitable material that surrounds the slit opening. There may also be a flap or a button to close the flap to prevent the heat or cold pack from being removed unless desired. The slits reinforcement should prevent the fabric from around the slit from stretching so that the compression does not weaken over use. This is particularly advantageous when the stretching of the compression fabric is generally transverse to the length of the slit, i.e. the direction away from the long length of the slit. The slit is preferably positioned just above the area of the higher compression so that the pack can be placed under the higher compression material or under the compression material without ruining the compression. The ends of the slit preferably have a rivet or button over the end to prevent the slit from becoming longer and thereby tearing the compression fiber. The grommet, button or rivet, etc. may be made of any suitable material. The pouch portion extending from the slit preferably contacts the skin or body contact layer of the brace.

In another embodiment the pouch has two layers. The outer layer is the compression material where the inner surface comprises one wall of the pouch. The other side of the pouch is the inside of the body contact layer in a two-layer structure. Alternatively, in a three-layer structure with a mesh outer compression layer, the compression layer and surface of the mesh layer are secured to form a pocket or pouch. The heat and cold can pass through the openings in the mesh toward the user. The body contact layer may be a fabric or other material that protects the body from damage due to the cold or heat.

Many of the braces because of the body shape have a top end and bottom end. The ends will have a generally horizontal portion as a bottom or top surface, see FIGS. 9 and 12. Alternatively, the braces may have a length extending from the top edge to the bottom edge, see FIG. 9. The slit is preferably at an angle to one of the top or bottom edges of the brace as well as at an angle to an imaginary line extending perpendicular to at least one of the top or bottom edges of the brace, see FIG. 9. More specifically, the slit is positioned so that it is preferably not parallel to one of the top or bottom edges of the brace and not parallel or perpendicular to the imaginary line extending the length of the brace.

The hot/cold pack utilized herein may also be formed to have a tab protruding from the end disposed nearest the opening into the pocket to assist in removal of the pack from the pocket due to the compression force trapping it therein as a result of the elasticity of the material used for the sleeve and pocket liner. The tab may also provide a convenient place to grasp the hot/cold pack after it has been heated in a microwave or cooled in a refrigerator/freezer. The hot/cold pack will be configured to stay at the designed temperature when applied to the wearer of the device for at least 12-15 minutes for cooling and for 15-20 minutes for application of heat, but which time may vary depending upon certain factors, such as the outside temperature, and the person's body temperature. The hot/cold packs may be stored in thermal isolation bags, which may also permit removal and subsequent usage in the pockets for use in intermittent hot/cold treatments for the wearer.

The pocket(s) may be formed by creating an opening in the side of the elastic sleeve 110 and by securing (e.g., by stitching, gluing, or ultrasonic high frequency welding) a liner to the interior of the sleeve. The liner material for the pocket may also be an elastic material, so that the pocket (and thus the hot and/or cold pack received therein) may be pressed up against the body of the wearer by the sleeve. The presence of the hot and/or cold pack therein may also serve to increase tension to the surrounding area and force more of the hot/cold pack into contact with the body of the wearer, to provide greater surface area of contact, and thereby aid in spreading the effect of the hot/cold treatment.

Figure 6:
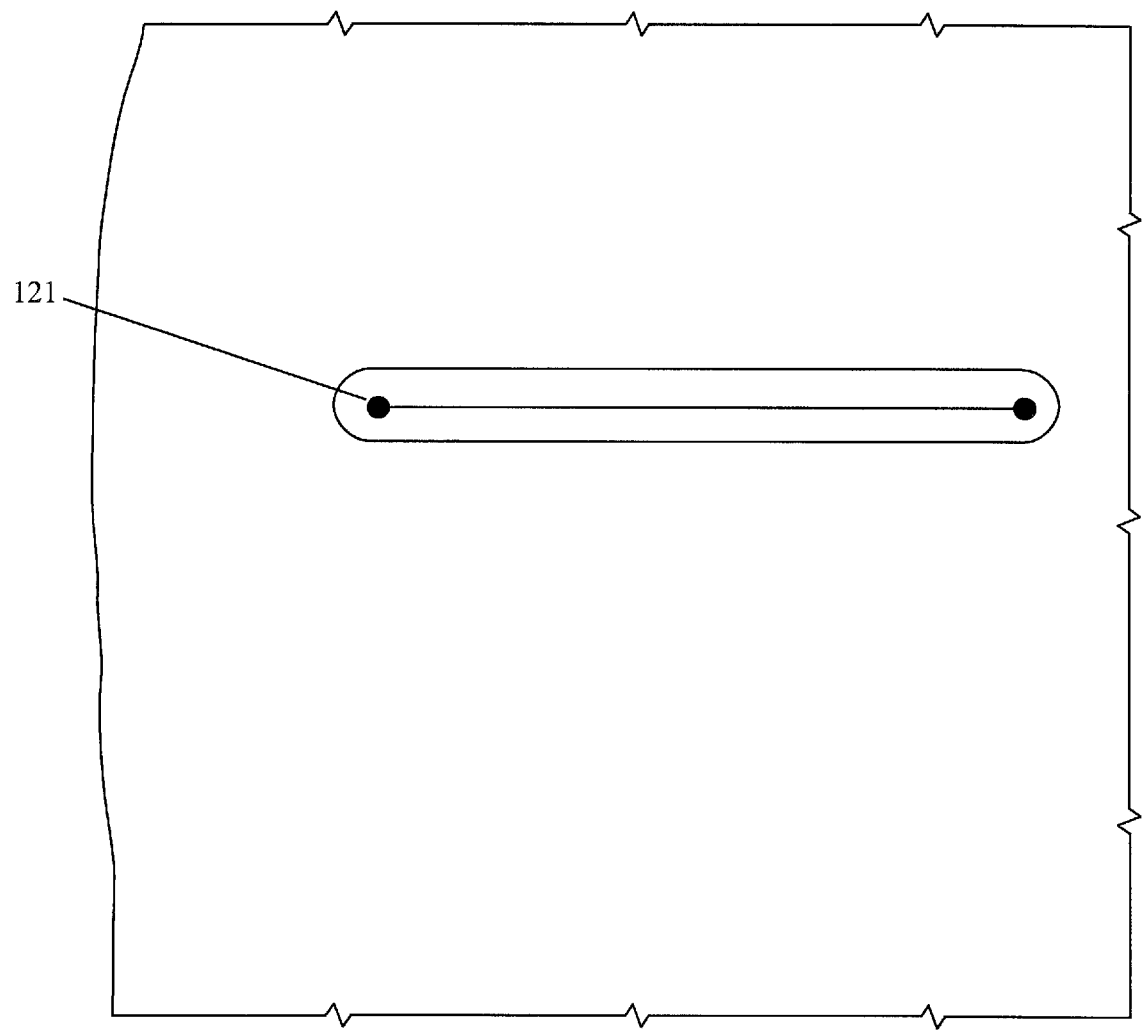
FIG. 6 is a view of a slit in a compression fabric with a pair of rivets at the ends of the slit to prevent the slit or tear from becoming larger or ripping the fabric.

The opening in the side of the elastic sleeve 110 may be reinforced in any suitable manner. In one embodiment the sides of the opening in the elastic sleeve 110 may be reinforced by stitching. In another embodiment the sides of the opening in the elastic sleeve 110 may be reinforced by a grommet 120 that may be secured to the outside of the sleeve in any suitable manner. In yet another embodiment, one grommet 120 may be placed against the outside of the sleeve and one grommet 120 may be placed against the inside of the sleeve, over the opening, and the two grommets may be secured to each other (e.g., by adhesive bonding, stitching, using rivets, etc.), and thus be secured to the sleeve. The grommet 120 may be made of any suitable, material including, but not limited to, a metal, a thermoplastic rubber, a thermoplastic polyurethane, etc. The use of a grommet 120 on the outside, and/or the use of grommets on both the outside and inside may each serve to prevent the opening formed in the elastic sleeve material from expanding locally. A rivet 121 may be used at the ends of the slit, as shown in FIG. 6.

This arrangement permits placement of a hot/cold pack into the pocket from outside of the brace, and therefore conveniently permits its removal and replacement with another hot/cold pack at any time by the wearer.

The elasticity of the pocket liner and of the sleeve may serve to keep the hot and/or cold pack from falling out. Alternatively or additionally, the elastic sleeve 110 may further include a closure apparatus to secure the opening into the pocket to positively retain the hot and/or cold pack therein. Such closure apparatus may be any suitable closure known in the art, including, but not limited to: buttons, snaps, hook and loop fastening materials (e.g., materials sold under the trade name "Velcro"), zippers, etc.

The pockets and hot/cold packs may have any desired shape. Preferably, the pockets and corresponding packs have a shape formed to correspond to the desired area of the body for which the brace is designed, and may also be shaped/sized to accommodate use of the springs. For example, as shown in FIG. 1, the elastic sleeve 110 may be formed to have a triangular shaped pocket that may extend into proximity to the X-shape of the first stiffening member 113 and second stiffening member 114 to form a generally triangular-shaped pocket.

Figure 4:
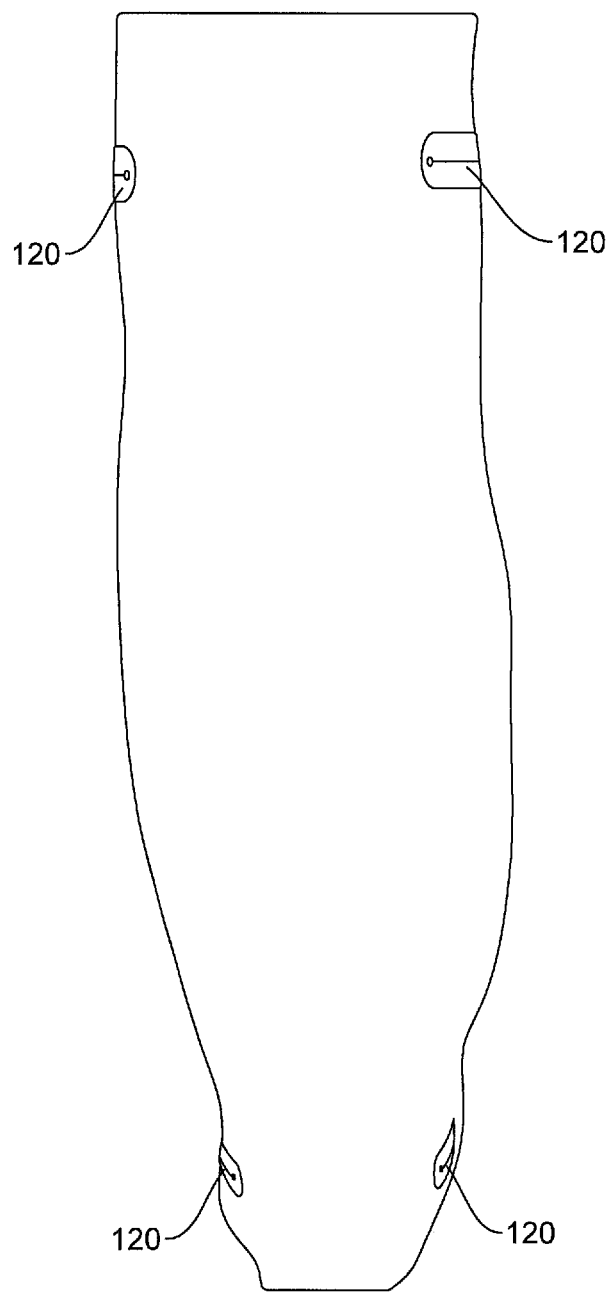
FIG. 4 is a side view of the brace shown in FIG. 3.
Figure 5:
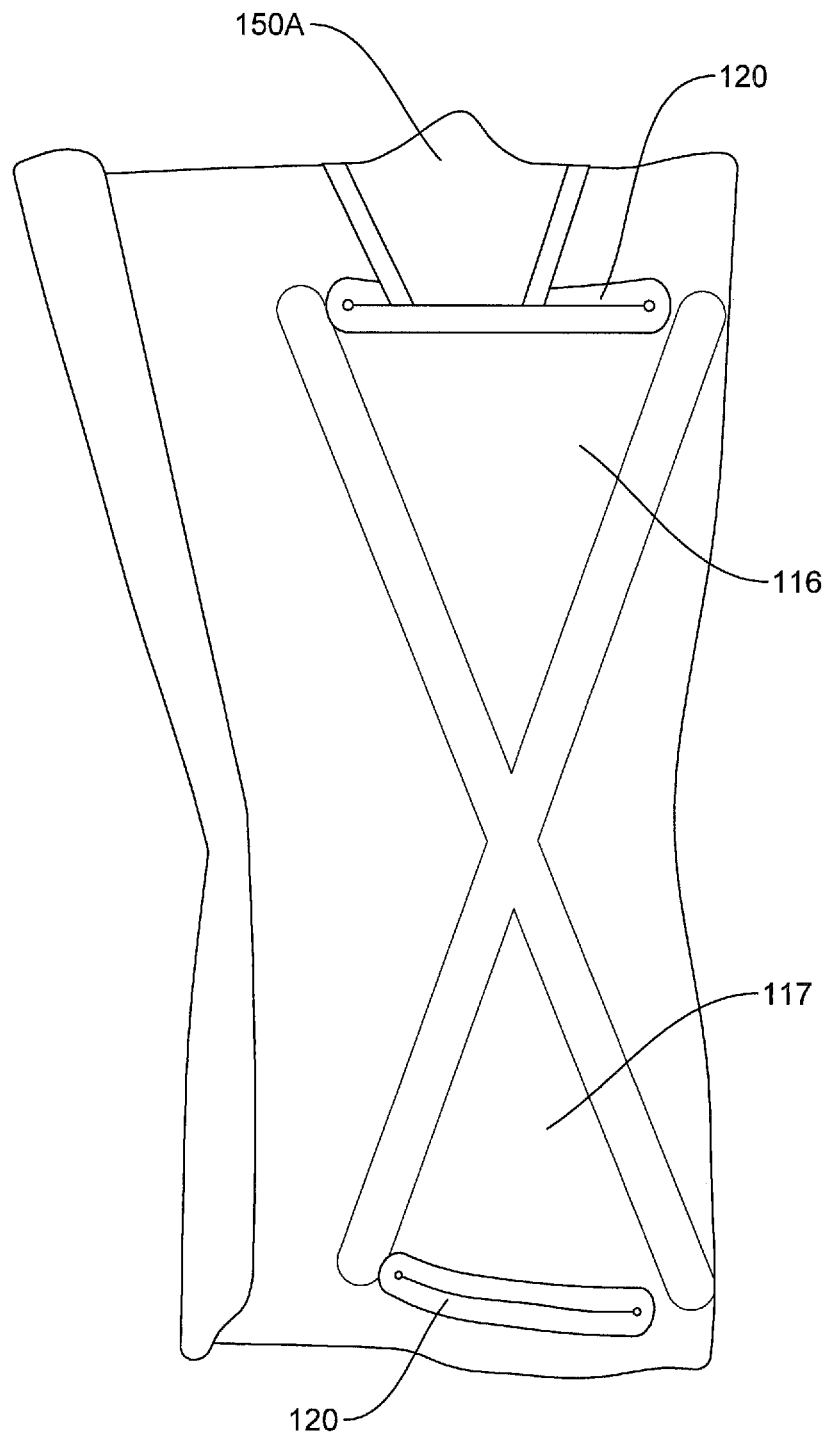
FIG. 5 is the front perspective view of FIG. 3, shown with one of the hot/cold packs being inserted into one of the pockets.

Also, the elastic sleeve 110 may be formed to have, for example, four such pockets-pockets 116, 117, 118, and 119 (see FIG. 4), two of which pockets may be on the left side of the brace and two of which may be on the right side of the brace (i.e., to be positioned on the left side and the right side of the leg).

Figure 3:
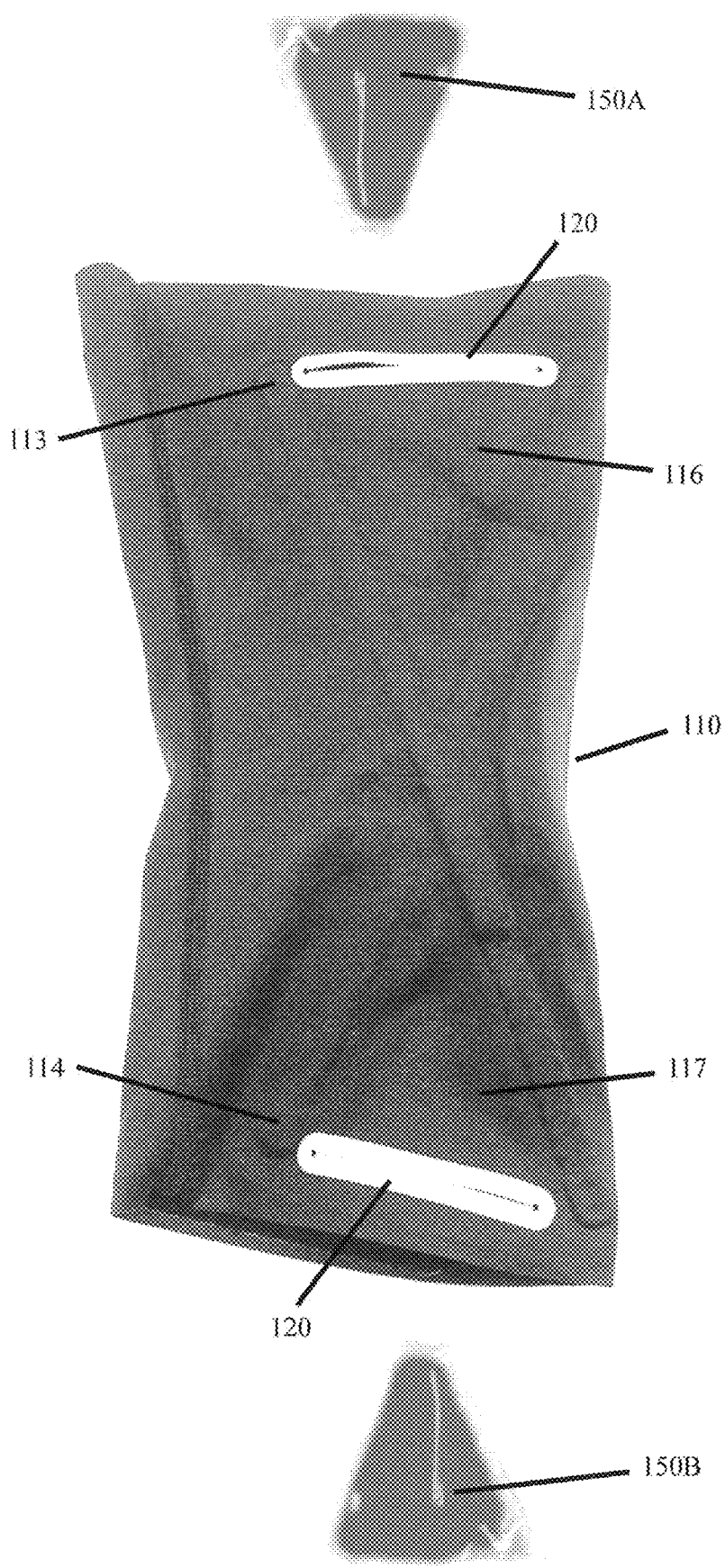
FIG. 3 is the front perspective view of FIG. 1, shown prior to inserting the hot/cold packs within the pockets of the brace.

The hot/cold packs may also be triangular-shaped, and as seen in FIG. 3, a triangular-shaped hot/cold pack 150A may be received within the pocket 116, while a triangular-shaped hot/cold pack 150B may be received within the pocket 117.

FIG. 1 shows the knee brace 100 after the triangular-shaped hot/cold pack 150A has been received within the pocket 116, and after the triangular-shaped hot/cold pack 150B has been received within the pocket 117.

Figure 2:
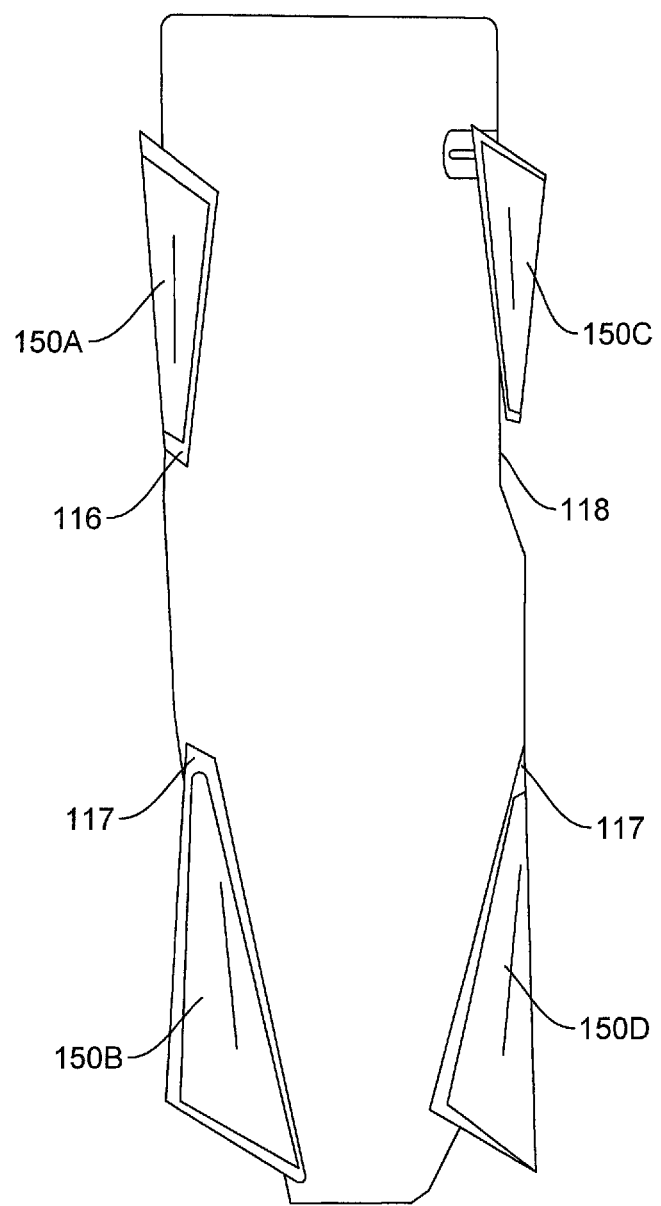
FIG. 2 is a side perspective view of the brace showing the arrangement of how hot/cold packs are positioned within each of four pockets of a brace, as shown in FIG. 1.

FIG. 2 shows the knee brace 100 after triangular-shaped hot/cold packs 150A, 150B, 150C and 150D have been respectively received within the pocket 116, 117, 118, and 119, and with the pocket cutaway to expose the packs.

As noted above, in other embodiments the pockets may be formed in an elastic sleeve of a brace for other parts of the body (e.g., an ankle brace with horse shoe shaped hot/cold packs, a lower leg brace, knee brace, leg strap, full leg, ¾ leg, hip, underwear, foot, back, waist, stomach, fingers, hand, wrist, forearm, elbow, full arm, shoulder, neck, top of head, short sleeve shirt, full sleeve shirt, shorts, full legged pants, etc.). Also, these braces may not require use of either the first stiffening member 113 or the second stiffening member 114 (or any stiffening member at all). The hot/cold packs that may be received in the pockets of any of those devices may provide for therapeutic effects (e.g., alleviating soreness and/or pain, reducing the effects of an existing injury, preventing a new injury, etc.). These inserts have been shown to reduce the effects of an injury by 50% to 90%, depending upon the location of use and the consistency of use. The pockets and stored hot/cold packs may be positioned to target muscle areas, tendons, and ligaments particularly where they attach to bone, and at other areas that are highly susceptible to injury.

The shapes and size of the pocket or pockets may be specifically designed for the purpose of each of the above devices, which may receive correspondingly shaped hot/cold packs.

While illustrative implementations of one or more embodiments of the disclosed apparatus are provided hereinabove, those skilled in the art and having the benefit of the present disclosure will appreciate that further embodiments may be implemented with various changes within the scope of the disclosed apparatus. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A knee brace comprising;
   a sleeve, said sleeve comprising an elastic material, said sleeve formed to fit on a leg of a wearer, and to extend a distance above the knee and extend a second distance below the knee;
   a first stiffening member;
   a second stiffening member;
   wherein said first stiffening member is coupled to said second stiffening member to crisscross to form an X-shape; and wherein said coupled first and second stiffening members are secured to a medial side of said sleeve, with its crisscrossed x-shape being centered proximate to a knee joint portion of said sleeve;
   a third stiffening member;
   a fourth stiffening member;
   wherein said third stiffening member is coupled to said fourth stiffening member to crisscross to form an X-shape; and wherein said coupled third and fourth stiffening members are secured to a lateral side of said sleeve with its crisscrossed x-shape being positioned centered proximate to said knee joint portion of said sleeve;
   a plurality of slits in said sleeve into a corresponding plurality of pockets;
   a plurality of thermal packs, with one of said thermal packs received in a respective one of said plurality of pockets;
   wherein said thermal packs are triangular shaped; and
   wherein said plurality of pockets are each triangular-shaped and respectively sized to receive one of said triangular shaped thermal packs therein in a clearance fit;
   wherein said plurality of pockets comprises four of said triangular-shaped pockets, two of said triangular-shaped pockets on said medial side of said sleeve, and two of said triangular-shaped pockets on said lateral side of said sleeve;
   wherein said two of said triangular-shaped pockets on said medial side are disposed in a respective triangular shape positioned between said x-shape of said first and second stiffening members; and
   wherein said two of said triangular-shaped pockets on said lateral side are disposed in a respective triangular shape positioned between said x-shape of said third and fourth stiffening members.

2. The knee brace according to claim 1, wherein said elastic material is an elastic material from the group of elastic materials consisting of: spandex, rubber, and latex.

3. The knee brace according to claim 2, wherein said coupled first and second stiffening members and said coupled third and fourth stiffening members are each respectively secured to said sleeve by being adhesive bonded thereto.

4. The knee brace according to claim 2, wherein said coupled first and second stiffening members and said coupled third and fourth stiffening members are each respectively secured to said sleeve by being sewn to the respective side of said sleeve between an outer layer and an inner layer of said sleeve.

5. The knee brace according to claim 2, wherein said coupled first and second stiffening members and said coupled third and fourth stiffening members are each respectively secured to said sleeve by positioning a respective cover layer over said stiffening members and stitching said respective cover layer to said sleeve.

6. The knee brace according to claim 1, wherein each said pocket comprises a liner, said liner comprising a mesh material.

7. The knee brace according to claim 6, wherein said mesh material is a mesh material from the group of mesh materials consisting of: a thermoplastic elastomer; and a thermoplastic polyurethane.

8. The knee brace according to claim 1, wherein said first and second stiffening members are fixedly coupled together to store energy when the user bends at the knee, and to utilize the stored energy to assist in lifting the user upward.

9. The knee brace according to claim 1, wherein said first and second stiffening members are pivotally coupled together, to pivot with respect to each other according to movements of the wearer's upper leg portion and lower leg portion at the knee joint.

10. The knee brace according to claim 1, wherein each of said stiffening members comprises an elongated metallic leaf spring.

11. The knee brace according to claim 1, wherein each said thermal pack is formed with a tab protruding from a base of said triangular shape, to assist in removal of said thermal pack from a corresponding said pocket.

12. The knee brace according to claim 1, wherein said sleeve comprises a reinforcement material around each said slit, said reinforcement material being a reinforcement material from the group of reinforcement materials consisting of: a grommet, an eyelet, stitching, one or more rivets, a printed silicon, and plastic material.

* * * * *